United States Patent [19]

Berg

[11] 4,080,075
[45] Mar. 21, 1978

[54] COMPENSATED DENSITOMETER

[75] Inventor: Bernard J. Berg, Grand Rapids, Mich.

[73] Assignee: Foresight Enterprises, Inc., Grand Rapids, Mich.

[21] Appl. No.: 724,742

[22] Filed: Sep. 20, 1976

[51] Int. Cl.² .................................... G01N 21/22
[52] U.S. Cl. .................... 356/202; 307/230; 328/145; 356/206
[58] Field of Search .............. 356/202, 203, 204, 206; 307/230; 328/145

[56] References Cited

U.S. PATENT DOCUMENTS

| | | | |
|---|---|---|---|
| 3,320,530 | 5/1967 | Pearlman | 328/145 |
| 3,528,749 | 9/1970 | Bower | 356/202 |
| 3,887,281 | 6/1975 | Kurita et al. | 356/206 |
| 3,918,815 | 11/1975 | Gadbois | 356/206 |
| 3,970,393 | 7/1976 | Krygeris et al. | 356/206 |

*Primary Examiner*—John K. Corbin
*Assistant Examiner*—R. A. Rosenberger
*Attorney, Agent, or Firm*—Glenn B. Morse

[57] ABSTRACT

The output of a test light of a densitometer is divided into a test beam and a reference beam. The test beam is caused to traverse film samples, and impinge on a detector that produces a signal responsive to the intensity of the received light. A second detector is arranged to receive the reference beam, which does not traverse the film sample. A measuring system is responsive to the output of the first detector, and utilizes the output of the second detector to compensate for variations in the intensity of the test light.

5 Claims, 4 Drawing Figures

COMPENSATED DENSITOMETER

BACKGROUND OF THE INVENTION

The maintenance of quality standards in X-ray photography requires precise control of exposure, source intensity, development procedures, and film characteristics, together with control of environmental variables. Monitoring of these factors is normally accomplished by measuring the density of the developed film by determining its light-transmission characteristics. This is done with an instrument commonly referred to as a densitometer. A beam of light from a standardized light source is caused to pass through a sample of the film, and a detector is positioned to respond to this light. The detector is normally a photo-voltaic device that produces a current output directly proportional to input light intensity over several orders of magnitude. This output is then delivered to a measuring system that converts input current to an output voltage, and a readout expressed as the logarithm of the ratio of the transmitted light through the film to the intensity of the transmitted light without the film being present. Standard procedure has currently involved the establishment of the light intensity without the film, as a matter of calibration. The film sample light transmission is then measured by the instrument, which usually yields a direct reading of the logarithm of the film transmission ratio, referred to as density.

These instruments have been subject to a variety of problems centering in the variation of the intensity of the test light source. Manufacturing variations, and the effects of heating and aging of the bulb components, are inevitably present, together with variations in the line voltage supplying the bulb. The latter are normally compensated for to some extent by either voltage regulation to a nominal level, or by feed back control of the lamp intensity by controlling the voltage on the lamp to eliminate fluctuations. These compensating arrangements have tended to become costly and power consuming, and to be rather ineffective in controlling all of the variables that produce alterations in the lamp brightness.

SUMMARY OF THE INVENTION

The present invention provides a test light output that is divided into a test beam and a reference beam. The test beam is caused to traverse the film sample, and impinge on a photo-voltaic detector producing a current output that is directed proportional to input light intensity. This detector output is then applied to an operational amplifier producing an output voltage related to the input current. A second detector is positioned to respond to the reference beam of light, which does not traverse the film sample. The output of this detector is applied to a second operational amplifier, and the outputs of both of these operational amplifiers are applied to a matched-pair transistor system producing a readout as the logarithm of the ratio of the transmitted light through the film to the light intensity on the same detector in the absence of the film. The output of the second operational amplifier is applied to the matched-pair transistor system to produce a current condition that is independent of variations in the brightness of the test light source.

DESCRIPTION OF THE PREFERRED EMBODIMENT

Figure 1:
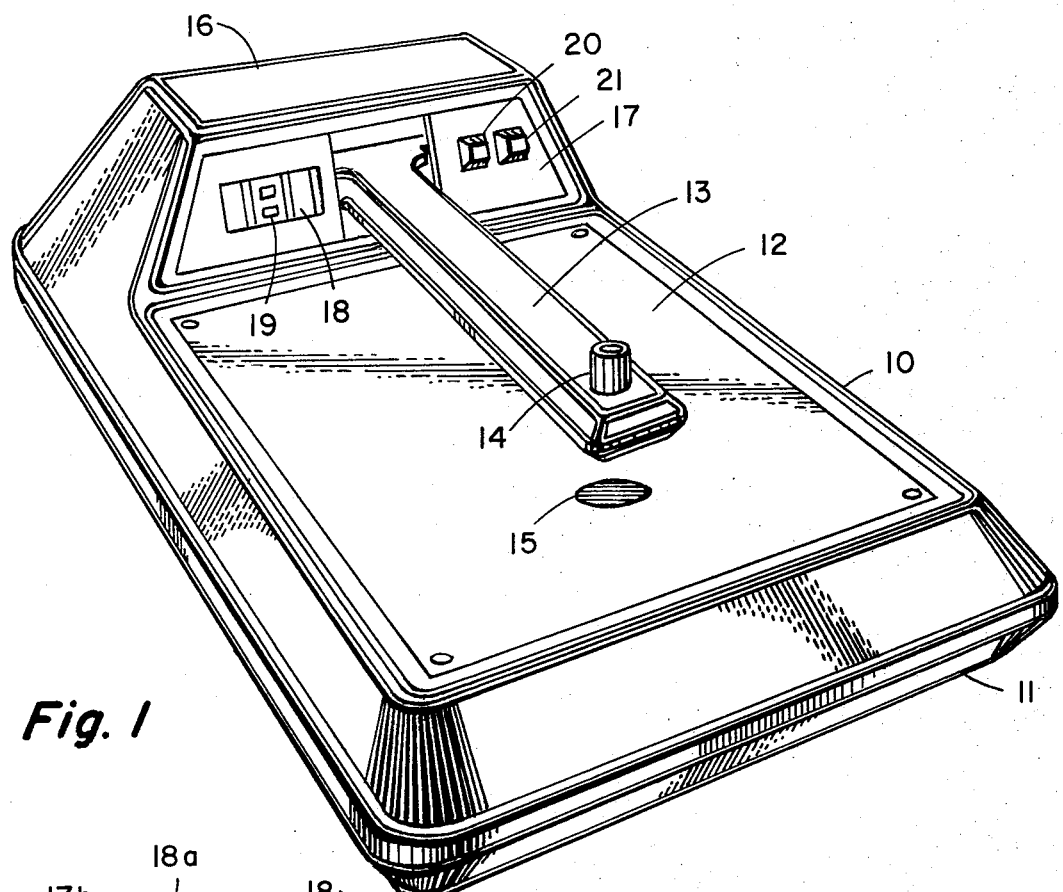
FIG. 1 is an exterior perspective view of a densitometer embodying the present invention.
Figure 2:
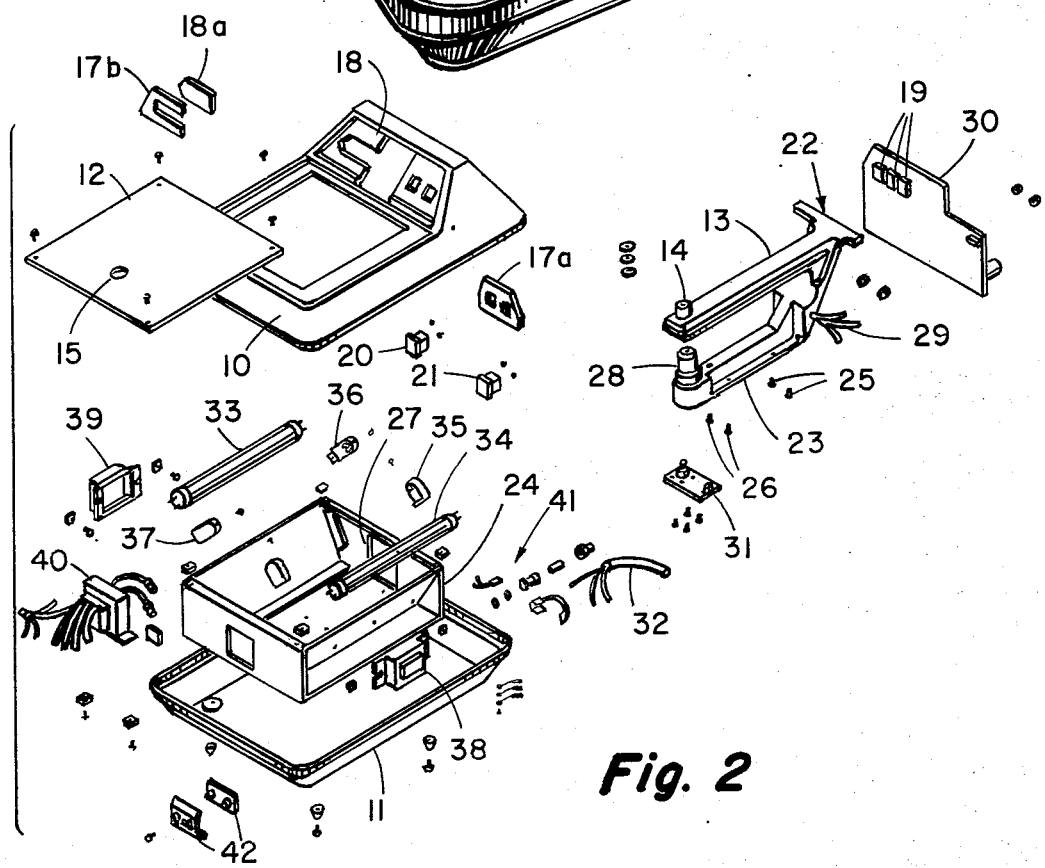
FIG. 2 is an exploded view showing the components of the device illustrated in FIG. 1.

The instrument illustrated in FIGS. 1 and 2 includes the upper housing section 10, the lower housing section 11, a translucent table panel 12, and an overarm 13. This cantilever member supports the detector unit 14 positioned directly above the opening 15 in the panel 12. The elevated portion 16 of the housing supports a front panel 17 providing an opening 18 for the window 18a through which the digital readout 19 is visible. The panel 17 also has openings for the control 20 of an off-on switch, and for the control 21 providing a null adjustment for the instrument. The cantilever overarm 13 is part of a U-shaped structure indicated generally at 22 in FIG. 2, with a base portion 23 normally secured to the bottom of the light box 24 attached to the bottom section 11 of the housing. Screws as shown at 25 and 26 traverse appropriately located holes in the bottom of the light box, and engage the lateral flange portions of the base 23, as shown in FIG. 2. The base 23 is assembled to the light box through the opening 27, and the integral construction of the member 22 assures the proper alignment of the test light 28 secured to the base section 23 of this member. This light, and the detector unit 14, may be considered as coaxial with the hole 15 in the translucent panel 12. Wiring as shown at 29 associates the test light 28 and the detector 14 with the principal circuitry of the instrument mounted on the printed circuit panels 30 and 31, together with the power provided through the exterior power cable 32. The panel 30 is mounted in the elevated section 16 of the housing, with the digital readout elements 19 in proper position for registry with the window 18.

In addition to the arm assembly 22, the light box 24 contains the fluorescent tubes 33 and 34 supported between the usual brackets as shown at 35–37 fastened in the usual manner to the walls of the light box 24. Conventional ballast assemblies as indicated at 38 and 39 are incorporated for association with these fluorescent tubes. Light from these tubes provides a general field of illumination underneath the translucent panel 12, so that a sample of film can be placed on this panel underneath the arm 13 for a general inspection of a photographic film, preparatory to selecting a particular area for placement directly under the detector 14. A transformer as shown at 40 is associated with the circuit supplying power to the test light system, derived from the incoming power cable 32 through the conventional assembly of fuses and connectors indicated generally at 41. The assembly indicated at 42 provides a clamping receptacle for the wire harness within the housing section 11 that electrically associates these components. The remaining items appeared in the exploded view of FIG. 2 are standard fastenings and devices shown in positions projected from their assembled relationship. The nameplate sections 17a and 17b may be considered as part of the panel generally indicated at 17 in FIG. 1. These may be integral, or separated as shown.

Figure 3:
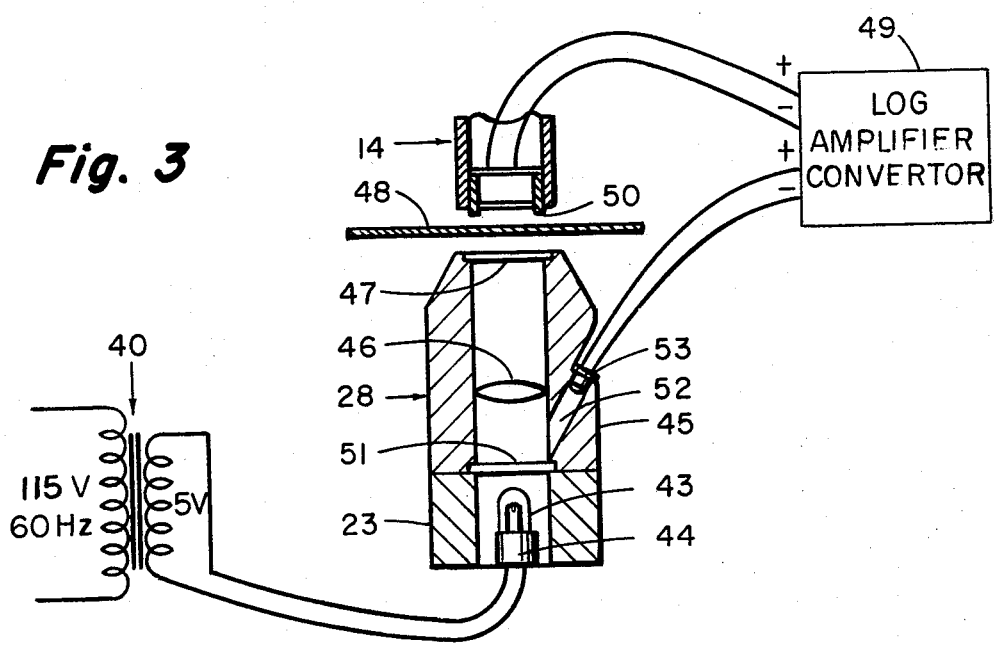
FIG. 3 is a schematic view showing the interrelationship of the components of the invention.

Referring to FIG. 3, the light unit 28 includes the bulb 43 having the base 44 fixed with respect to the section 23 of the arm assembly 22. The tubular extension 45 positions the lens 46 for collimating the light from the source 43, which is projected through the aperture plate 47, and then through the film sample 48. The detector, or light sensor, 14 receives whatever light traverses the film 48, and provides a response signal delivered to the measurement system indicated schematically at 49 in FIG. 3. The annular rubber seal 50 is incorporated to block off light from surrounding sources, as well as confine the light traversing the film 48. A color filter 51 is preferably incorporated in the assembly, and retained between the member 23 and the extension 45.

Light emerging from the filter 51 may be considered as the test light source. A part of this light proceeds through the lateral passage 52, and is received by the sensor-detector 53 as a reference light beam, with the response of the sensor 53 to this beam being delivered to the measuring system 49 to compensate for variations in the intensity of the bulb 43. The light tranversing the film 48 may be considered as the test beam, which is monitored in conjunction with the reference beam to provide a compensated indication of the density of the film sample 48.

Figure 4:
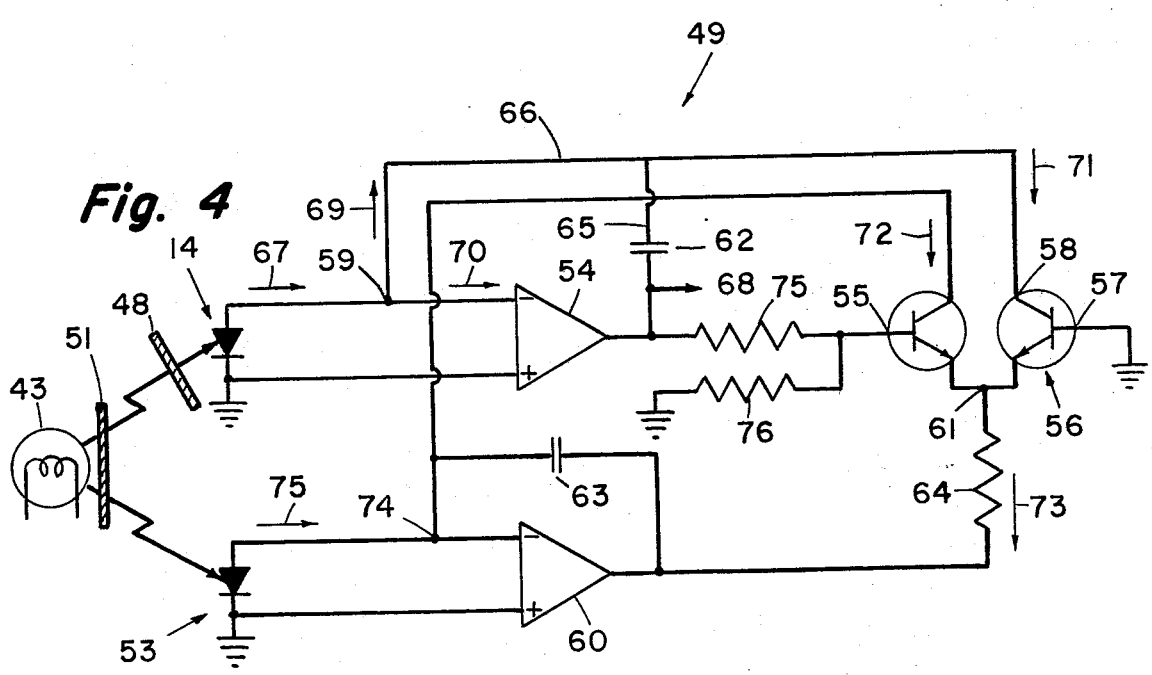
FIG. 4 is a circuit diagram of the arrangement shown in general terms in FIG. 3.

Referring to FIG. 4, the output of the detector 14 is applied to the input terminals of the operational amplifier 54, the output of which is applied to the base terminal 55 of the matched-pair transistor unit generally indicated at 56. The opposite base terminal 57 is grounded, as shown. The collector terminal 58 is directly connected to the point 59 associated with the input lead of the operational amplifier 54.

The second operational amplifier 60 receives the output of the reference sensor-detector 53, with the output of this amplifier being supplied to the emitter terminal 61 of the matched-pair transistor 56. The capacitors indicated at 62 and 63 limit the high frequency gain of the operational amplifiers to prevent oscillation. The resistor 64 limits the maximum current into the matched-pair of transistors, and controls high frequency gain.

The operational amplifier 54 functions in feedback relationship, as a result of the connection through the capacitor 62, the lead 65, and the lead 66. The current from the detector 14 is indicated at 67, and the effect of the circuit relationships involving the operational amplifier 54 and the matched-pair transistor 56 is to cause the measurement-indicating voltage at 68 to respond to satisfy the requirement that the currents indicated at 67, 69, and 70 should equal zero with respect to the point 59.

The characteristic of a matched-pair transistor is that a logarithmic voltage impressed across the two base leads produces a linear collector current response. If the current 67 increases by a given amount, the operational amplifier senses the imbalance between the current 67 and the current 69, and drives the voltage at 68 more negative. The differential voltage across the matched-pair transistor is then increased by $$\Delta E_{68} \frac{R_{76}}{R_{75}+R_{76}}$$

This causes the collector current $I_{71}$ to increase by $\Delta I_{71}$ until $\Delta I_{71} = \Delta I_{67}$. The voltage required to generate $\Delta I_{71}$ is:

$$R_{76} \frac{\Delta E_{68}}{R_{75}+R_{76}} = K_L \log \frac{I_{75}}{\Delta I_{71}}$$

The output (readout) voltage at 68 is thus a logarithmic function of $I_{75}/I_{71}$.

Operational amplifier 60 controls the total current through both sides of the matched-pair transistor 56, which is approximately the total of the currents 71 and 72. If the current 71 is increased, then the current 73 includes the currents 71 and 72, together with the amount of the increase in the current 71, so that the sum of the currents at the point 74 shall remain equal to zero. With this arrangement, if the current 75 from the reference sensor 53 increases, both sensors will produce an equal percentage of increased current. The logarithmic relationship of the readout voltage at 68 is thus unaltered, as is indicated by the following:

$$E_{68_1} = K \cdot \log I_{67}/I_{75},$$

where K is a constant, expressed in volts, relating amplifier output to the logarithm of the current ratios. Thus, $$E_{68_1} = K[\log I_{67} - \log I_{75}]$$

Then:

$$E_{68_2} = K[\log I_{67}(I+\Delta) - \log I_{75}(I+\Delta)] = K[\log I_{67} + \log(I+\Delta) - \log I_{75} - \log(I+\Delta)]$$

Therefore:

$$E_{68_2} = K\ [\log I_{67} - \log I_{75}]) = E_{68_1}$$

Although the above discussion concerns transmission densitometry, it also applies to relection densitometry.

I claim:

1. A system for measuring the light-transmission characteristics of a film, including a light source, a photo-voltaic sensor, means for supporting a film sample in a position interposed between said light source and sensor, and indicating means adapted to generate a signal that is a function of the output of said sensor wherein the improvement comprises:
    a second photo-voltaic sensor disposed to receive light from said light source along a path that does not traverse the said position of said film sample;
    first operational amplifier means operatively associated with said first sensor in feedback relationship;
    second operational amplifier means, operatively associated with said second sensor in feedback relationship; and
    matched-pair transistor means, and first circuit means operative to apply the output voltage of said first operational amplifier means across the base terminals of said matched-pair transistor means, and second circuit means operative to apply the output voltage of said second operational amplifier means between the emitter and one collector of said matchedpair transistor means, the other collector thereof being connected to the output of said first photo-voltaic detector.

2. A system as defined in claim 1, additionally including capacitor means in shunt relationship, respectively, with said operational amplifier means.

3. A system as defined in claim 1, additionally including first resistor means in series relationship with said first operational amplifier and said transistor means, and second resistor means in series relationship between ground and a point interposed between said first resistor means and said transistor means.

4. A system as defined in claim 1, additionally including resistor means in series relationship between said second operational amplifier and said transistor means.

5. A system as defined in claim 1, additionally including capacitor means in shunt relationship, respectively, with said operational amplifier means, and further including first resistor means in series relationship with said first operational amplifier and said transistor means, and second resistor means in series relationship between ground and a point interposed between said first resistor means and said transistor means, and third resistor means in series relationship between said second operational amplifier and said transistor means.

* * * * *